(12) United States Patent
Radjy

(10) Patent No.: US 10,983,106 B2
(45) Date of Patent: *Apr. 20, 2021

(54) SYSTEMS, APPARATUS AND METHODS FOR TESTING AND PREDICTING THE PERFORMANCE OF CONCRETE MIXTURES

(71) Applicant: QUIPIP, LLC, Pittsburgh, PA (US)

(72) Inventor: Farrokh F. Radjy, Pittsburgh, PA (US)

(73) Assignee: QUIPIP, LLC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/574,343

(22) Filed: Sep. 18, 2019

(65) Prior Publication Data
US 2020/0011846 A1 Jan. 9, 2020

Related U.S. Application Data

(63) Continuation of application No. 15/680,827, filed on Aug. 18, 2017, now Pat. No. 10,458,971, which is a continuation of application No. 15/008,098, filed on Jan. 27, 2016, now Pat. No. 9,766,221.

(60) Provisional application No. 62/110,040, filed on Jan. 30, 2015.

(51) Int. Cl.
*G01N 33/38* (2006.01)
*G01N 25/20* (2006.01)

(52) U.S. Cl.
CPC ........... *G01N 33/383* (2013.01); *G01N 25/20* (2013.01)

(58) Field of Classification Search
CPC .............................. G01N 33/383; G01N 25/20
See application file for complete search history.

(56) References Cited

U.S. PATENT DOCUMENTS

| 3,423,219 A | 1/1969 | Eick |
| 3,678,753 A | 7/1972 | Eggleston |
| 4,272,824 A | 6/1981 | Lewinger |
| (Continued) | | |

FOREIGN PATENT DOCUMENTS

| CN | 204255517 U | 4/2015 |
| GB | 2268801 A | 1/1994 |
| (Continued) | | |

OTHER PUBLICATIONS

Parikh, Pranav, Process Modeling and Automation of Concrete Cylinder Testing, NCSU Libraries, Mar. 21, 2007, 48 pgs., http://repository.lib.ncsu.edu/ir/bitstream/1840.16/2494/1/etd.pdf.

(Continued)

*Primary Examiner* — Brandi N Hopkins
*Assistant Examiner* — Janice M Soto
(74) *Attorney, Agent, or Firm* — Lucas & Mercanti, LLP

(57) ABSTRACT

A mobile calorimeter includes a container comprising one or more walls defining a cavity. The container is adapted to hold a concrete mixture within the cavity. The mobile calorimeter also includes one or more heat flow sensors adapted to detect a heat flow generated by the concrete mixture. The heat flow sensors may include a thermoelectric device, a Peltier plate, or a macro fiber composite (MFC) sensor. The one or more heat flow sensors may be attached to the one or more walls, or may be embedded within the one or more walls. Data relating to a heat flow is obtained by the heat flow sensors, and is used to generate a prediction of a characteristic or performance of the concrete mixture.

10 Claims, 12 Drawing Sheets

(56) References Cited

U.S. PATENT DOCUMENTS

| | | |
|---|---|---|
| 4,398,427 A | 8/1983 | Pan |
| 4,433,385 A | 2/1984 | DeGasperi |
| 4,440,717 A | 4/1984 | Bevilacqua |
| 4,515,545 A | 5/1985 | Hinriches |
| 4,538,467 A | 9/1985 | Stoll |
| 4,548,507 A | 10/1985 | Mathis |
| 4,566,806 A | 1/1986 | DeBondt |
| 4,603,395 A | 7/1986 | Steinberger |
| 4,604,706 A | 8/1986 | Fisher, Jr. |
| 4,715,726 A | 12/1987 | Tsuruta |
| 4,816,131 A | 3/1989 | Bomsztyk |
| 4,822,431 A | 4/1989 | Bricher |
| 4,881,819 A | 11/1989 | Blees |
| 4,900,360 A | 2/1990 | Whitescarver |
| 4,902,211 A | 2/1990 | Svanholm |
| 4,943,930 A | 7/1990 | Radjy |
| 4,966,463 A | 10/1990 | Hihara |
| 5,041,987 A | 8/1991 | Kuwahara |
| 5,316,701 A | 5/1994 | Payne |
| 5,333,969 A | 8/1994 | Blaha |
| 5,437,181 A | 8/1995 | Nasser |
| H001560 H | 7/1996 | Gill |
| 5,541,855 A | 7/1996 | Enzler |
| 5,552,995 A | 9/1996 | Sebastian |
| 5,615,573 A | 4/1997 | Lee |
| 5,621,648 A | 4/1997 | Crump |
| 5,665,254 A | 9/1997 | Isono |
| 5,943,234 A | 8/1999 | Martinez |
| 5,983,165 A | 11/1999 | Minnich |
| 6,057,773 A | 5/2000 | Shukla |
| 6,064,982 A | 5/2000 | Puri |
| 6,186,654 B1 | 2/2001 | Gunteret, Jr. |
| 6,198,980 B1 | 3/2001 | Costanza |
| 6,223,094 B1 | 4/2001 | Muehleck |
| 6,224,250 B1 | 5/2001 | Kreinheder |
| 6,324,904 B1 | 12/2001 | Ishikawa |
| 6,343,285 B1 | 1/2002 | Tanaka |
| 6,527,438 B2 | 3/2003 | Zollinger |
| 6,536,060 B1 | 3/2003 | Janssens |
| 6,604,493 B1 | 8/2003 | Toki |
| 6,642,906 B1 | 11/2003 | Machalek |
| 6,687,559 B2 | 2/2004 | Radjy |
| 6,915,216 B2 | 7/2005 | Troxler |
| 6,958,693 B2 | 10/2005 | Rothgeb |
| 6,966,687 B1 | 11/2005 | Elefsrud |
| 7,021,123 B2 | 4/2006 | Wallevik |
| 7,089,816 B2 | 8/2006 | Hakimuddin |
| 7,092,893 B2 | 8/2006 | Megan |
| 7,192,397 B2 | 3/2007 | Lewkowicz |
| 7,201,866 B2 | 4/2007 | Stallone |
| 7,173,538 B2 | 6/2007 | Pedraza |
| 7,333,148 B2 | 2/2008 | Chang |
| 7,343,212 B1 | 3/2008 | Brearley |
| 7,386,368 B2 | 6/2008 | Andersen |
| 7,409,853 B2 | 8/2008 | Bilberger |
| 7,551,058 B1 | 6/2009 | Johnson |
| 7,568,835 B2 | 8/2009 | Pils |
| 7,621,186 B2 | 11/2009 | Heathman |
| 7,672,921 B1 | 3/2010 | Clay |
| 7,708,944 B1 | 5/2010 | Sadik |
| 7,755,971 B2 | 7/2010 | Heatley |
| 7,777,628 B2 | 8/2010 | Tilson, Jr. |
| 7,804,406 B2 | 9/2010 | Kaga |
| 7,841,249 B2 | 11/2010 | Tormoen |
| 7,974,723 B2 | 7/2011 | Moyne |
| 7,987,728 B2 | 8/2011 | Song |
| 8,020,431 B2 | 9/2011 | Cooley |
| 8,230,738 B2 | 7/2012 | Radziszewski |
| 8,280,697 B2 | 10/2012 | Thiel |
| 8,397,810 B2 | 3/2013 | Verret |
| 8,428,913 B2 | 4/2013 | Troxler |
| 8,462,343 B2 | 6/2013 | Rao |
| 8,491,717 B2 | 7/2013 | Koehler |
| 8,661,909 B2 | 3/2014 | Chu |
| 8,794,078 B2 | 8/2014 | Darbe |
| 8,829,365 B1 | 9/2014 | Wallace |
| 8,881,809 B2 | 11/2014 | Verret |
| 8,939,020 B2 | 1/2015 | Townsend |
| 9,040,000 B2 | 5/2015 | Dinges |
| 9,082,147 B2 | 7/2015 | Radjy |
| 9,194,855 B2 | 11/2015 | Radjy |
| 9,254,583 B2 | 2/2016 | Radjy |
| 9,321,398 B2 | 4/2016 | Radjy |
| 9,593,988 B1* | 3/2017 | Liberman ............... G01K 17/00 |
| 2002/0010525 A1 | 1/2002 | Radjy et al. |
| 2002/0015354 A1 | 2/2002 | Buckelew |
| 2002/0078979 A1 | 6/2002 | Aulbers |
| 2002/0147665 A1 | 10/2002 | Tillery |
| 2003/0006907 A1 | 1/2003 | Lovegreen |
| 2003/0069795 A1 | 4/2003 | Boyd |
| 2003/0145043 A1 | 7/2003 | Matuska |
| 2003/0154143 A1 | 8/2003 | Chen |
| 2003/0221485 A1 | 12/2003 | Toki |
| 2003/0227394 A1 | 12/2003 | Rothgeb |
| 2004/0004554 A1 | 1/2004 | Srinivasan |
| 2004/0010334 A1 | 1/2004 | Bickley |
| 2004/0039504 A1 | 2/2004 | Coffee |
| 2004/0107141 A1 | 6/2004 | Conkel |
| 2004/0252745 A1 | 12/2004 | Park |
| 2005/0004733 A1 | 1/2005 | Pillar |
| 2005/0017873 A1 | 1/2005 | Liu |
| 2005/0056415 A1 | 3/2005 | Zillinger |
| 2005/0132782 A1* | 6/2005 | Wallevik ............... B01F 7/063 |
| | | 73/54.28 |
| 2005/0149377 A1 | 7/2005 | Schierholt |
| 2005/0166803 A1 | 8/2005 | Dillenbeck |
| 2005/0187744 A1 | 8/2005 | Morrison |
| 2005/0204825 A1 | 9/2005 | Kunerth |
| 2005/0210995 A1 | 9/2005 | Drnevich |
| 2005/0219940 A1 | 10/2005 | Elefsrud |
| 2007/0046479 A1 | 3/2007 | Hines |
| 2007/0056481 A1 | 3/2007 | Gray |
| 2007/0096880 A1 | 5/2007 | Nagai |
| 2007/0112860 A1 | 5/2007 | Ostanik |
| 2007/0116402 A1 | 5/2007 | Slade |
| 2007/0145973 A1 | 6/2007 | Bertozzi |
| 2007/0179653 A1 | 8/2007 | Trost |
| 2008/0028988 A1 | 2/2008 | Welker |
| 2008/0041173 A1 | 2/2008 | Tormoen |
| 2008/0067228 A1 | 3/2008 | Kaga |
| 2008/0127742 A1 | 6/2008 | Mueller |
| 2008/0221815 A1 | 9/2008 | Trost |
| 2008/0264459 A1 | 10/2008 | Wobben |
| 2008/0316856 A1 | 12/2008 | Cooley |
| 2009/0037026 A1 | 2/2009 | Sostaric |
| 2009/0072978 A1 | 3/2009 | Tilson, Jr. |
| 2009/0171595 A1 | 7/2009 | Bonilla Benegas |
| 2009/0177482 A1 | 7/2009 | Granruth |
| 2009/0211754 A1 | 8/2009 | Verret |
| 2010/0024518 A1 | 2/2010 | Radziszewski |
| 2010/0042389 A1 | 2/2010 | Farruggia |
| 2010/0161364 A1 | 6/2010 | Lokowandt |
| 2010/0161365 A1 | 6/2010 | Lokowandt |
| 2010/0161366 A1 | 6/2010 | Clemens |
| 2010/0246312 A1 | 9/2010 | Welker |
| 2010/0252946 A1 | 10/2010 | Stumm |
| 2011/0004332 A1 | 1/2011 | Andersen |
| 2011/0004333 A1 | 1/2011 | Andersen |
| 2011/0115613 A1 | 5/2011 | Kaga |
| 2011/0305115 A1 | 12/2011 | Jiang |
| 2012/0016523 A1 | 1/2012 | Koehler |
| 2012/0142017 A1 | 6/2012 | Park |
| 2012/0152025 A1 | 6/2012 | Chu |
| 2012/0173171 A1 | 7/2012 | Bajwa |
| 2012/0204625 A1 | 8/2012 | Beaupre |
| 2012/0221379 A1 | 8/2012 | Martinez |
| 2012/0298010 A1 | 11/2012 | Ginn |
| 2013/0053284 A1* | 2/2013 | Jamison ............... G01N 33/24 |
| | | 507/200 |
| 2013/0151428 A1 | 6/2013 | Hesse |
| 2014/0137646 A1* | 5/2014 | Troxler ............... E01C 19/00 |
| | | 73/32 R |

(56) References Cited

U.S. PATENT DOCUMENTS

| | | |
|---|---|---|
| 2014/0150542 A1 | 6/2014 | Townsend |
| 2014/0214627 A1 | 7/2014 | Radjy |
| 2014/0222209 A1 | 8/2014 | Radjy |
| 2014/0241104 A1 | 8/2014 | Phares |
| 2014/0270623 A1 | 9/2014 | Ahmed |
| 2015/0078417 A1 | 3/2015 | Verdino |
| 2015/0109287 A1 | 4/2015 | Grichnik |
| 2015/0140673 A1 | 5/2015 | Bruno |
| 2015/0142336 A1 | 5/2015 | Sant |
| 2015/0212061 A1 | 7/2015 | Radjy |
| 2015/0213459 A1 | 7/2015 | Radjy |
| 2015/0247833 A1 | 9/2015 | Radjy |
| 2015/0287125 A1 | 10/2015 | Radjy |
| 2016/0018383 A1 | 1/2016 | Radjy |

FOREIGN PATENT DOCUMENTS

| | | |
|---|---|---|
| JP | 2006-023106 A | 1/2006 |
| JP | 2011-063955 A | 3/2011 |
| KR | 10-2007-0042255 A | 4/2007 |
| KR | 10-2008-0072955 A | 8/2008 |
| KR | 10-2009-0038179 A | 4/2009 |
| KR | 10-2009-0114162 A | 11/2009 |
| SU | 736002 A1 | 5/1980 |
| WO | 9204679 A1 | 3/1992 |
| WO | 9535415 A1 | 12/1995 |
| WO | 9930265 A1 | 6/1999 |
| WO | 0016210 A1 | 3/2000 |

OTHER PUBLICATIONS

Al-Roos, Said Ibrahim Abu, SCADA Online Product Quality Control, Islamic University of Gaza, Oct. 2013, 90 pgs., http://library.iugaza.edu.ps/thesis/112422.pdf.

Mulkern, Matthew, Smart Aggregates Containing Piezoceramics: Fabrication and Applications, NSF—REU Program Smart Aggregates Report, Aug. 2, 2007, 11 pgs.

3D-printed Smart Cap Uses Electronics to Sense Spoiled Food, CYTOFLUIDIX Microfluidics Technology Review, Aug. 23, 2015, 3 pgs.

Wood, Chris, UC Berkeley's Smart Cap Can Detect Spoiled Milk, Jul. 24, 2015, 1 pg.

Black, T., Paving the Road to the 21st Century, American City & County, Nov. 1997, vol. 12, No. 12, pp. 44-49.

Black, T., Warming Up to Technology, American City & Country, Apr. 1998, vol. 113, No. 4, pp. 64-79.

Malloy, C., EPA Cites Recovery Potential in Flowable Fill, Concrete Products, Nov. 1998, vol. 101, No. 11, pp. 61-62 (partial article).

Obla, Karthik H., Specifying Fly Ash for Use in Commerce, Concrete InFocus, Spring 2008, pp. 60-66.

Taylor, Peter C., Can We Really Measure Cement Content in Hardened Concrete and Mortar? Concrete.com, Feb. 2, 2009, 6 pgs.

PCT dated Aug. 10, 2017 from corresponding International Application No. PCT/US2016/015143.

International Search Report dated Mar. 31, 2016 from corresponding International Application No. PCT/US2016/015143.

Written Opinion of the International Searching Authority dated Mar. 31, 2016 from corresponding International Application No. PCT/US2016/015143.

\* cited by examiner

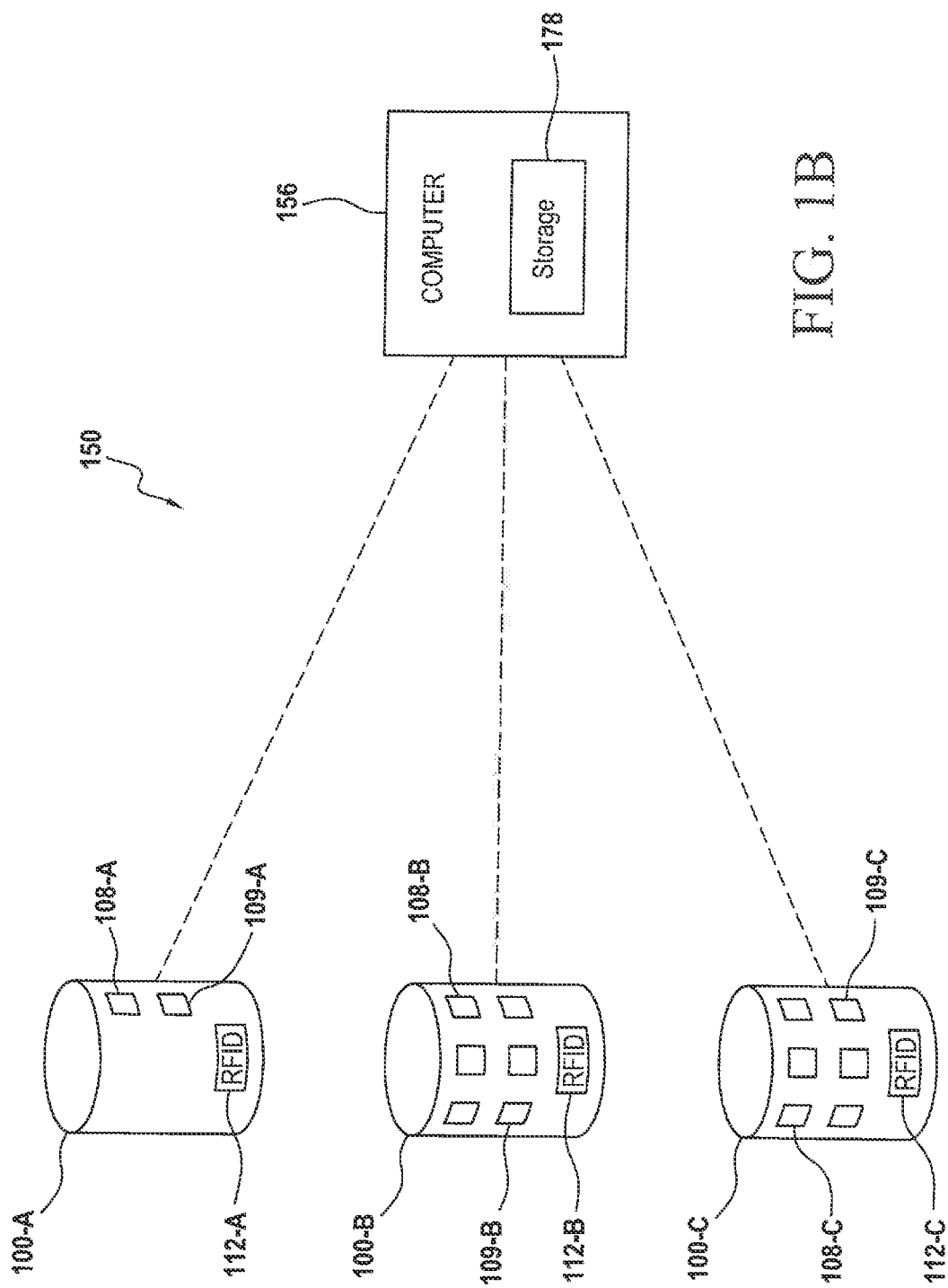

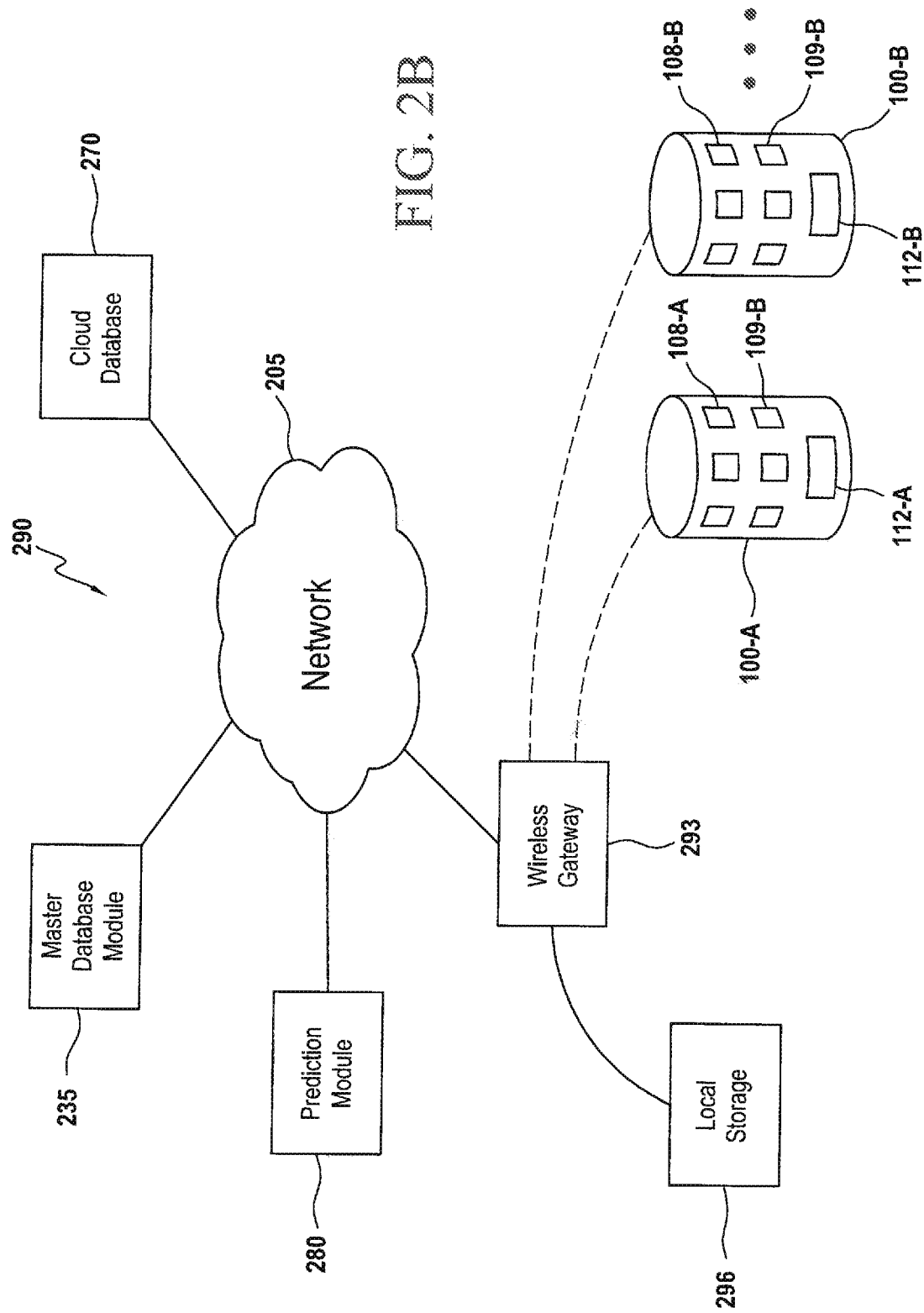

SYSTEMS, APPARATUS AND METHODS FOR TESTING AND PREDICTING THE PERFORMANCE OF CONCRETE MIXTURES

CROSS-REFERENCE TO RELATED APPLICATIONS

This application is a continuation of U.S. application Ser. No. 15/680,827, filed Aug. 18, 2017, which is a continuation of U.S. application Ser. No. 15/008,098, filed Jan. 27, 2016, now U.S. Pat. No. 9,766,221 issued Sep. 19, 2017, which claimed the priority of Provisional Application Ser. No. 62/110,040 filed Jan. 30, 2015, the priority of all applications is claimed and all applications are incorporated herein by reference.

TECHNICAL FIELD

This invention relates generally to the production and testing of concrete, and more particularly to systems, apparatus, and methods for testing and predicting the performance of concrete mixtures.

BACKGROUND

Concrete is generally used within the industry to refer to a mixture of cement, sand, stone, and water which upon aging turns into a hardened mass. The term concrete, as used in the specification and claims herein, means not only concrete as it is generally defined in the industry (cement, sand and stone), but it also means mortar (cement, sand and water) and cement(cement and water which hardens into a solid mass upon aging).

In the construction field, after a batch of concrete has been produced for use at a particular site, it is useful to be able to predict certain performance characteristics such as the in-place strength of the batch. Accurate prediction of concrete performance can increase the quality of the end product, and can provide other benefits such as allowing the use of accelerated construction schedules.

Several methods for testing and monitoring in-place strength of a concrete mass have been incorporated into the American Standard Testing Methods, including ASTM C805 (The Rebound Number Method—the so-called Swiss Hammer Method), ASTM C597 (The Pulse Velocity (Sonic) Method), and ASTM C900 (The Pullout Strength Method).

There is an ongoing need for improved systems and methods for measuring and predicting the strength and performance of concrete.

SUMMARY

In accordance with an embodiment, a mobile calorimeter includes a container having one or more walls defining a cavity, the container adapted to hold a concrete mixture within the cavity, and one or more heat flow sensors adapted to generate data relating to a heat flow generated by the concrete mixture.

In one embodiment, the mobile calorimeter also includes a second container adapted to hold concrete and to fit inside the container.

In another embodiment, the one or more heat flow sensors include a thermoelectric device, a Peltier plate, or a macro fiber composite (MFC) sensor.

In another embodiment, the one or more heat flow sensors are attached to the one or more walls. Alternatively, the one or more heat flow sensors may be embedded within the one or more walls.

In another embodiment, the container has one of a cylindrical shape, a cubical shape, and a rectangular shape.

In another embodiment, the mobile calorimeter also includes a radio frequency identification tag.

In another embodiment, the mobile calorimeter also includes a humidity sensor, a temperature sensor, a motion sensor, or a GPS-based location sensor.

In another embodiment, a system includes a mobile calorimeter, and a processor adapted to receive the data from the one or more heat flow sensors and generate a prediction of a characteristic of the concrete mixture, based on the data.

In accordance with another embodiment, a method of controlling the quality of one or more batches of a concrete mixture includes performing the following series of steps for each of a plurality of batches of concrete produced in a closed-loop production system: pouring a portion of the respective batch of concrete into a mobile calorimeter that comprises a heat flow sensor and a radio-frequency identification device (RFID), receiving from the RFID an identifier associated with the respective mobile calorimeter, receiving from the heat flow sensor a signal indicating that the mobile calorimeter is full of concrete, receiving from the heat flow sensor one or more measurements of heat flow, determining data defining an expected setting behavior and an expected strength of the respective batch of concrete based on the one or more measurements of heat flow, and storing the one or more measurements of heat flow and the data in association with the identifier.

In another embodiment, the mobile calorimeter also includes a humidity sensor, a temperature sensor, a motion sensor, or a location sensor.

In another embodiment, the mobile calorimeter includes a location sensor. Location data is received from the location sensor, and a location of the mobile calorimeter is determined based on the location data.

In accordance with another embodiment, a method of testing a performance of a batch of concrete includes using a heat flow sensor to obtain a measure of heat flow generated by a quantity of concrete, the quantity of concrete being obtained from a batch of concrete, and determining a measure of an expected performance of the batch of concrete, based on the measure of heat flow.

These and other advantages of the present disclosure will be apparent to those of ordinary skill in the art by reference to the following Detailed Description and the accompanying drawings.

BRIEF DESCRIPTION OF THE DRAWINGS

FIG. 1B shows a concrete testing system in accordance with an embodiment;

FIG. 2B shows a concrete testing system in accordance with another embodiment;

DETAILED DESCRIPTION

In accordance with an embodiment, a mobile calorimeter is provided. The mobile calorimeter includes a container comprising one or more walls defining a cavity, the container adapted to hold a quantity of concrete within the cavity, and one or more heat flow sensors. Each of the heat flow sensors may be, for example, a thermoelectric device, such as a Peltier plate, adapted to generate a voltage in response to a heat flow. Each heat flow sensor may be a macro fiber composite (MFC) sensor adapted to detect a heat flow.

Figure 1A:
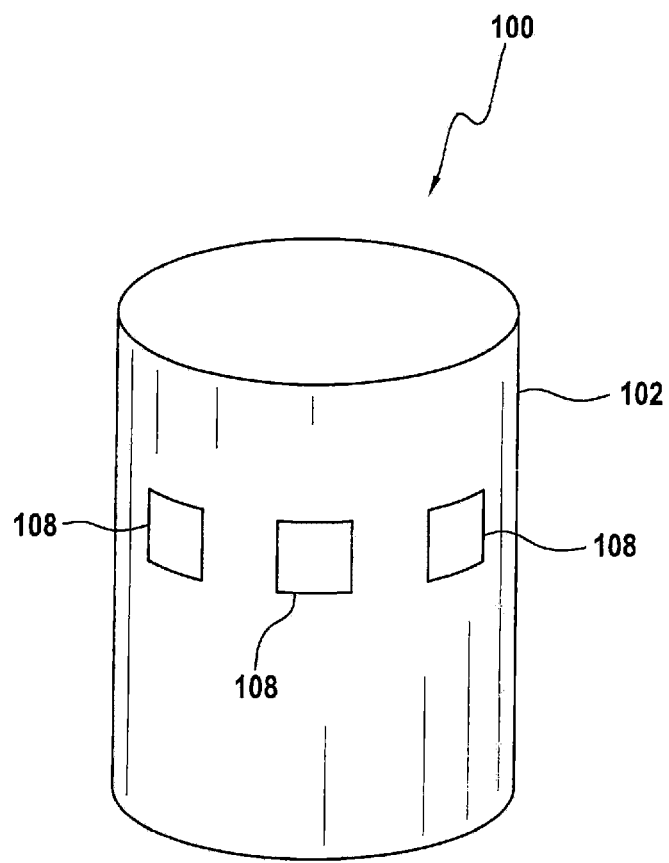
FIG. 1A shows a mobile calorimeter in accordance with an embodiment.

FIG. 1A shows a mobile calorimeter 100 in accordance with an embodiment. Mobile calorimeter 100 includes a cylinder 102 into which a selected quantity of concrete mixture may be poured. For example, cylinder 102 may be a standard 4×8-inch or 6×12-inch test cylinder. Alternatively, cylinder 102 may be larger and may hold, for example, up to 200 gallons of concrete, or more. Preferably, mobile calorimeter 100 is small enough to be readily moved from one location (e.g., a construction site) to another.

In other embodiments, a mobile calorimeter may be any container having a plurality of walls defining a cavity capable of holding a quantity of concrete. Thus, a mobile calorimeter may have other shapes. For example, a mobile calorimeter may be a cube or a rectangular shaped container.

Mobile calorimeter 100 includes one or more heat flow sensors 108. In the illustrative embodiment, heat flow sensors 108 are attached to the walls of mobile calorimeter 100. In another embodiment, heat flow sensors 108 are embedded within the walls of mobile calorimeter 100. Heat flow sensors 108 are adapted to generate a measure of heat flow. Each heat flow sensor 108 may be a thermoelectric device such as a Peltier plate, adapted to generate a voltage in response to a heat flow. Each heat flow sensor 108 may be a macro fiber composite (MFC) sensor adapted to detect a heat flow.

Mobile calorimeter 100 may also include a transmitter, a receiver, or a transceiver for transmitting and/or receiving data, or otherwise have communication capability. For example, a heat flow sensor 108 may include a transmitter, receiver, or transceiver. Mobile calorimeter 100 may transmit data wirelessly, for example.

One or more mobile calorimeters may be used to gather information concerning various batches of concrete used in a construction project. FIG. 1B shows a concrete testing system 150 in accordance with an embodiment. Concrete testing system 150 includes a plurality of mobile calorimeters 100-A, 100-B, 100-C, which may be located at a construction site, for example. A quantity of a concrete mixture is poured into one or more of mobile calorimeters 100-A, 100-B, 100-C.

Each mobile calorimeter 100-A, 100-B, 100-C includes one or more heat flow sensors 108-A, 108-B, 108-C. Each heat flow sensor 108 may include a thermoelectric device, an MFC sensor, etc., adapted to detect and measure heat flow. Each mobile calorimeter 100-A, 100-B, 100-C also includes one or more sensors 109, which may include other types of sensors such as GPS-based location detectors, motion detectors, humidity sensors, temperature sensors, etc. Mobile calorimeters 100-A, 100-B, 100-C also includes radio-frequency identification (RFID) tags 112-A, 112-B, 112-C.

Each RFID tag 112 transmits a unique identifier associated with its respective mobile calorimeter 100.

Concrete testing system 150 also includes a computer 156 which includes a storage 178. Mobile calorimeters 100 transmit information to computer 156, which stores the information in storage 178. In one embodiment, mobile calorimeters 100 transmit information wirelessly, via a Wi-Fi network.

For example, when mobile calorimeter 100-A is used, RFID 112-A of mobile calorimeter 100-A may transmit to computer 156 an identifier of mobile calorimeter 100-A. A sensor 109-A attached to mobile calorimeter 100-A may include a GPS-based location sensor; the sensor 109 may transmit location data indicating the location of mobile calorimeter 100-A to computer 156. Mobile calorimeter 100-A has a single heat flow sensor 108-A. Heat flow sensor 108-A may obtain and transmit heat flow data to computer 156. Computer 156 may store the identifier of mobile calorimeter 100-A, the location data obtained by sensor 109-A, and the heat flow data obtained by heat flow sensors 108-A, in database 178. Computer 156 may be located locally (e.g., at the construction site) or at a remote location.

Figure 2A:
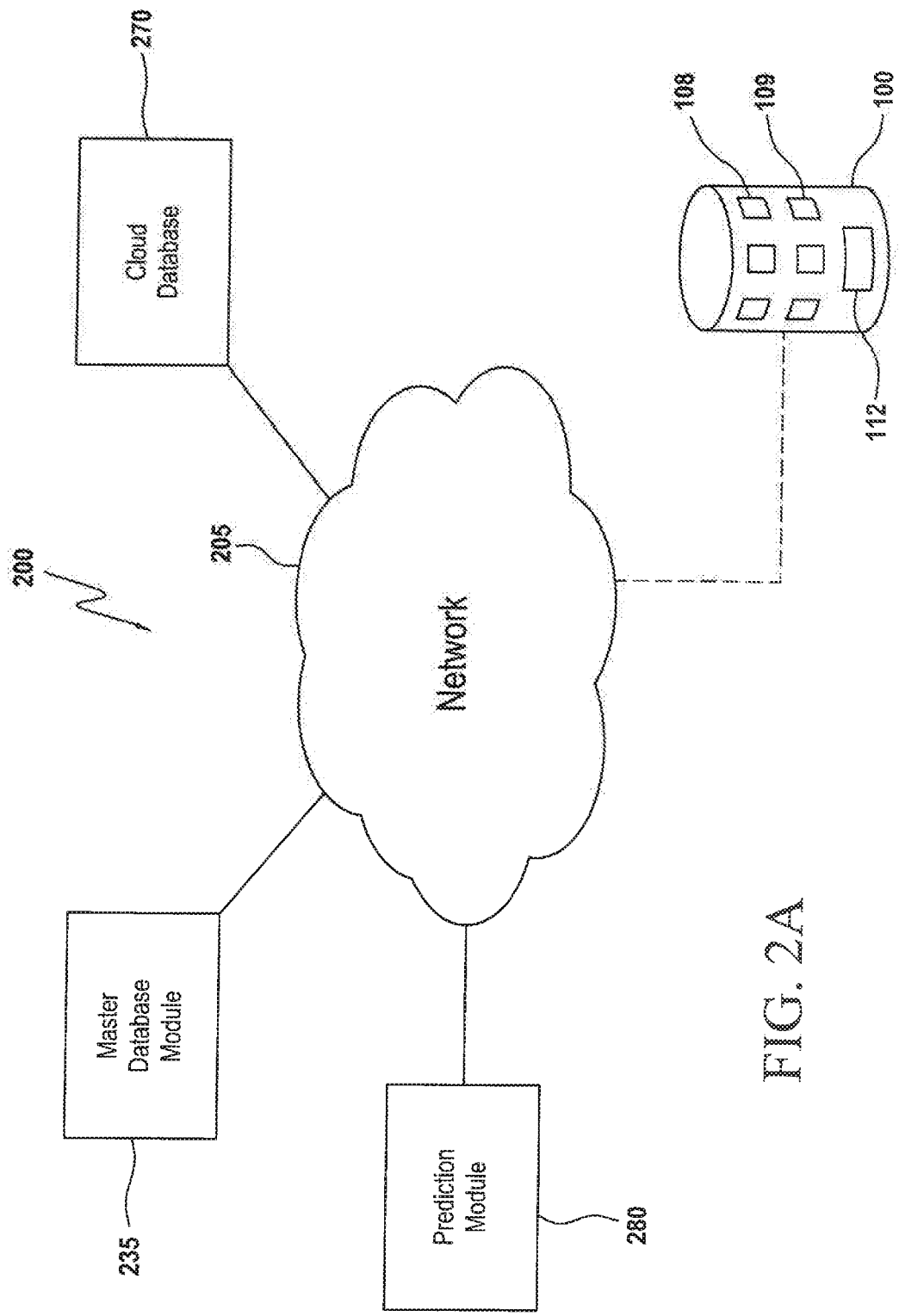
FIG. 2A shows a concrete testing system in accordance with another embodiment.

FIG. 2A shows a concrete testing system in accordance with another embodiment. Concrete testing system 200 includes mobile calorimeter 100, a network 205, a master database module 235, a prediction module 280, and a cloud database 270. Master database module 235 and cloud database 270 process and store various types of data and may reside and operate on a server computer, for example. Prediction module 280 may also reside and operate on a server computer. While one mobile calorimeter is shown in FIG. 2A, concrete testing system 200 may include more than one mobile calorimeter.

In the embodiment of FIG. 2A, network 205 is the Internet. In other embodiments, network 205 may comprise one or more of a number of different types of networks, such as, for example, an intranet, a local area network (LAN), a wide area network (WAN), a wireless network, a Fibre Channel-based storage area network (SAN), or Ethernet. Other networks may be used. Alternatively, network 205 may comprise a combination of different types of networks.

In the illustrative embodiment, mobile calorimeter 100 includes heat flow sensors 108, sensors 109, and RFID 112. Heat flow sensors 108, sensors 109, and RFID 112 are linked to network 205. Heat flow sensors 108 and sensors 109 gather information related to a batch of concrete and transmit the information to master database module 235 via network 205. Mobile calorimeter 100 may transmit data to network 205 wirelessly, for example.

Prediction module 280 analyzes data obtained by heat flow sensors 108, and data obtained by sensors 109, with respect to the particular batch of concrete, and generates data indicating an expected performance of the batch. For example, prediction module 280 may project setting behavior and strength for the batch based on heat flow data generated by heat flow sensors 108, or based on other data. Methods for projecting the setting behavior and strength of concrete are known.

In another embodiment, mobile calorimeter 100 may include a MFC sensor; the data obtained by the MFC sensor may be used for other purposes. For example, master database module 235 may use data obtained by an MFC sensor on mobile calorimeter 100 to determine when mobile calorimeter 100 is being filled with concrete, when mobile calorimeter 100 is filled with concrete, and/or when mobile calorimeter 100 is being moved.

FIG. 2B shows a concrete testing system in accordance with another embodiment. Concrete testing system 290 includes a plurality of mobile calorimeters including mobile calorimeters 100-A, 100-B, etc. Concrete testing system 290 also includes network 205, master database module 235, prediction module 280, and cloud database 270, which correspond to components shown in FIG. 2A. Accordingly, master database module 235 and cloud database 270 process and store various types of data and may reside and operate on a server computer, for example. Prediction module 280 may also reside and operate on a server computer. While two mobile calorimeters are shown in FIG. 2B, concrete testing system 290 may include any number of mobile calorimeters.

Concrete testing system 290 also includes a wireless gateway 293, which is connected to network 205. Wireless gateway 293 communicates wirelessly with mobile calorimeters 100-A, 100-B, etc. Thus a mobile calorimeter such as mobile calorimeter 100-A may transmit data via wireless gateway and network 205 to master database module 235 or to prediction module 280, for example. Concrete testing system 290 also includes a local storage 296, which is linked to wireless gateway 293. Wireless gateway 293 may from time to time store data in local storage 296.

In an illustrative example, concrete testing system 200 or concrete testing system 290 may be utilized to monitor and control the quality of various batches of concrete delivered to one or more construction sites. Referring again to FIG. 2B, suppose, for example, that a portion of a batch of a concrete mixture is poured into mobile calorimeter 100-A. In accordance with an embodiment, heat flow measurements relating to the concrete mixture in mobile calorimeter 100-A may be obtained and used to generate a prediction of a performance or characteristic of the concrete mixture.

Figure 3A:
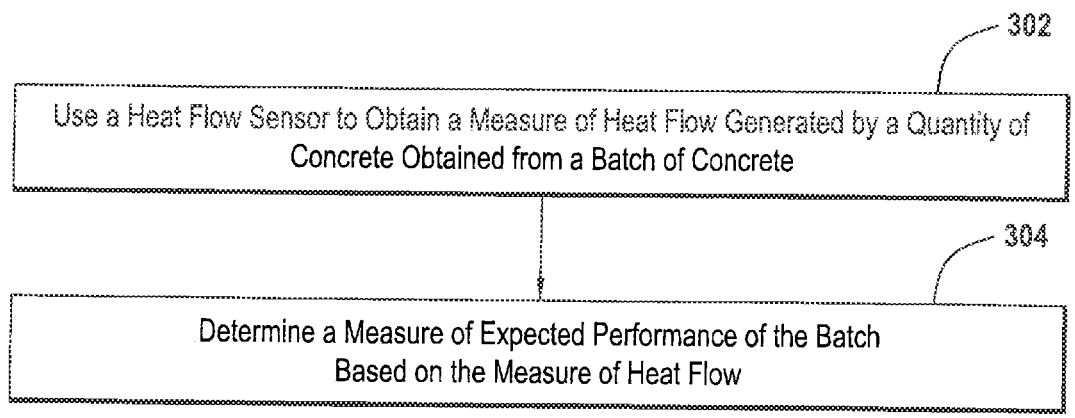
FIG. 3A is a flowchart of a method of determining a measure of expected performance of a batch of a concrete mixture in accordance with an embodiment.

FIG. 3A is a flowchart of a method of testing a batch of concrete in accordance with an embodiment. At step 302, a heat flow sensor is used to obtain a measure of heat flow generated by a quantity of concrete obtained from a batch of concrete. For example, heat flow sensor 108-A of mobile calorimeter 100-A may obtain a measure of a heat flow generated by the concrete mixture in mobile calorimeter 100-A. Mobile calorimeter 100-A transmits the heat flow data via wireless gateway 293 and network 205 to master database module 235. Master database module 235 transmits the heat flow data to prediction module 280.

At step 304, a measure of expected performance of the batch is determined, based on the measure of heat flow. Prediction module 280 generates a predicted performance or predicted characteristic of the concrete mixture, based on the heat flow data received from mobile calorimeter 100-A. For example, prediction module 280 may generate a prediction of the strength of the concrete mixture based on the heat flow data.

Figure 3B:
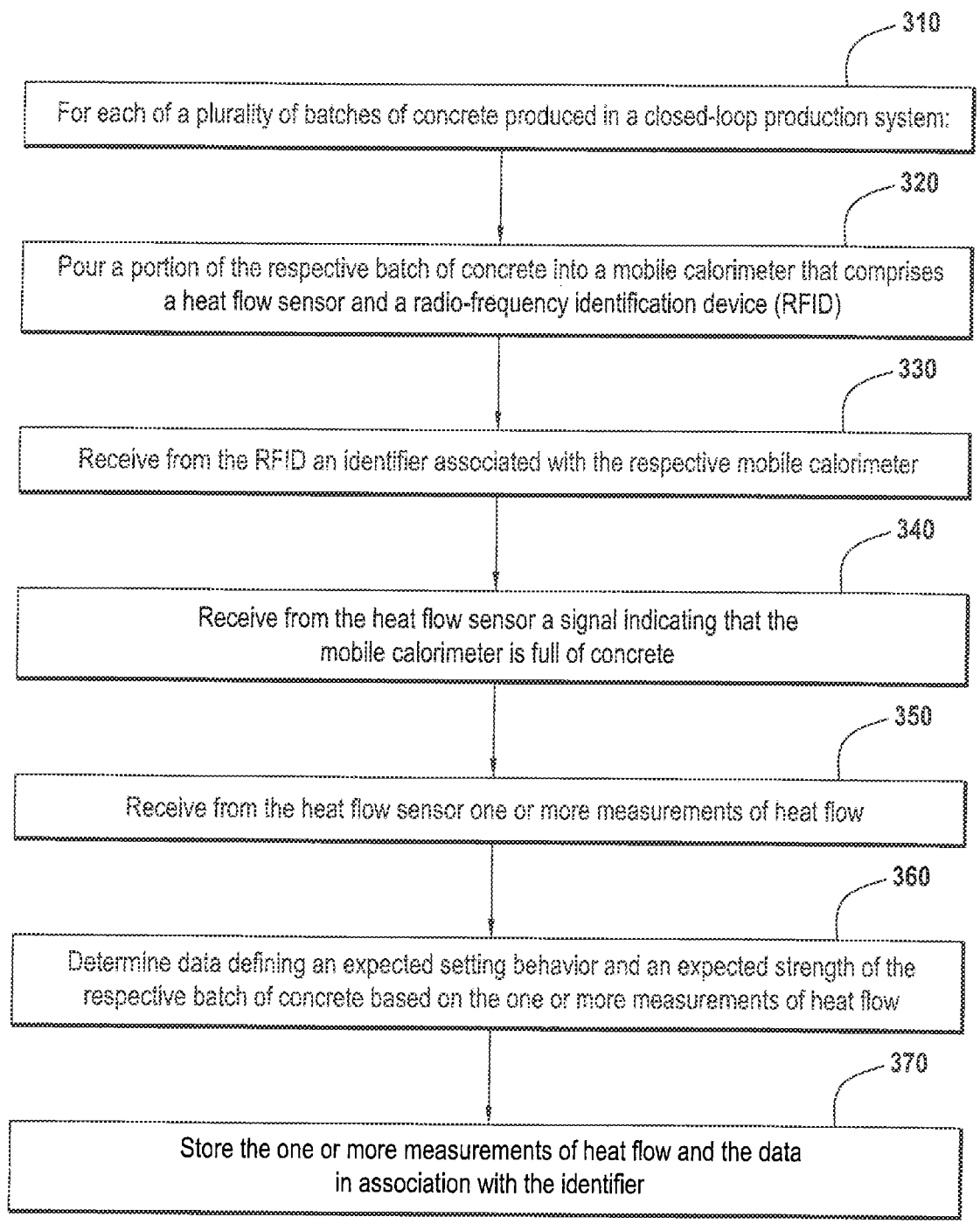
FIG. 3B is a flowchart of a method of determining a measure of expected performance of a batch of a concrete mixture in accordance with another embodiment.

FIG. 3B is a flowchart of a method of testing the quality of a batch of a concrete mixture in accordance with another embodiment. In the illustrative embodiment, it is supposed that multiple batches of concrete are produced at a production facility (or at multiple facilities), and delivered to one or more construction sites. The production facilities may be part of a closed-loop production system, for example.

Referring to block 310, for each of a plurality of batches of concrete produced in a closed-loop production system, a series of steps is performed. For purposes of illustration, the steps are described with respect to a single batch of concrete.

A batch (truckload) of concrete is mixed at a production facility according to a desired formula and transported to a selected site. At step 320, a portion of the respective batch of concrete is poured into a mobile calorimeter that comprises a heat flow sensor and a radio-frequency identification tag (RFID). Referring to the illustrative embodiment of FIG. 2A, for example, when the truck carrying the batch of concrete arrives at the site, mobile calorimeter 100 is retrieved. In order to test the concrete mixture, a portion of the batch of concrete is poured into the mobile calorimeter 100. Heat flow sensors 108, sensors 109 and RFID 112 on the mobile calorimeter are activated, as necessary. RFID 112 transmits the unique identifier of mobile calorimeter 100. A GPS-based location detector on the mobile calorimeter 100 generates and transmits location data.

At step 330, an identifier associated with the respective mobile calorimeter is received from the RFID. Master database module 235 receives and stores the identifier received from RFID 112, and any other data received from sensors on the mobile calorimeter 100. For example, master database module 235 may generate and store in cloud database 270 a data structure associated with the identifier, such as an object having a plurality of attributes, and store the data structure. Alternatively, a database or other structure may be used to store data.

At step 340, a signal indicating that the mobile calorimeter is full of concrete is received from the heat flow sensor. In the illustrative embodiment, heat flow sensors 108 detect when calorimeter 100 is full and transmit an alert to master database module 235. In one embodiment, in response to the signal, master database module 235 causes the truck to stop pouring concrete.

As the concrete in mobile calorimeter 100 sets, various measurements are obtained. In particular, at step 350, one or more measurements of heat flow are received from the heat flow sensor. Thus, heat flow sensors 108 detect heat flow generated by the hydration heat as the concrete sets, and transmits the data to the master database module 235.

At step 360, data defining an expected setting behavior and an expected strength of the respective batch of concrete is determined based on the one or more measurements of heat flow. For example, master database 235 may provide the heat flow information received from heat flow sensors 108 to prediction module 280. Prediction module 280 projects setting behavior and strength for the batch of concrete, based on the heat flow information, and provides such prediction data to master database module 235.

At step 370, the one or more measurements of heat flow and the data are stored in association with the identifier. Master database module 235 may store the identifier of the batch, the data received from sensors 108, data received from other sensors 109, and the prediction data generated by prediction module 280, in storage. For example, master database module 235 may store information in cloud database 270. Master database module 235 may store the information in connection with the object associated with the identifier.

In one embodiment, data generated by sensors 108 is continually subject to statistical analysis to generate real-time projections, control charts, etc.

Sensors 109 may obtain and transmit other types of data to master database module 235. For example, sensors 109 may transmit location data, time data, etc., to master database module 235. Sensors 109 may also detect motion data and inform master database module 235. Sensors 109 may also detect temperature and humidity data, and air-related data, and transmit the data to master database module 235. For example, in one embodiment, mobile calorimeter 100 includes a GPS-based location sensor. Master database module 235 may receive location-related data from the location sensor and determines at which construction site the mobile calorimeter is located, where at the construction site the mobile calorimeter is located, etc. Prediction module 280 may determine expected performance characteristics of the concrete mixture based on such data received from sensors 109.

In another embodiment, one or more of the sensors on a particular mobile calorimeter may transmit a unique identifier associated with the sensor. Master database module 235 may use the unique identifier of a sensor to identify the mobile calorimeter.

Figure 4A:
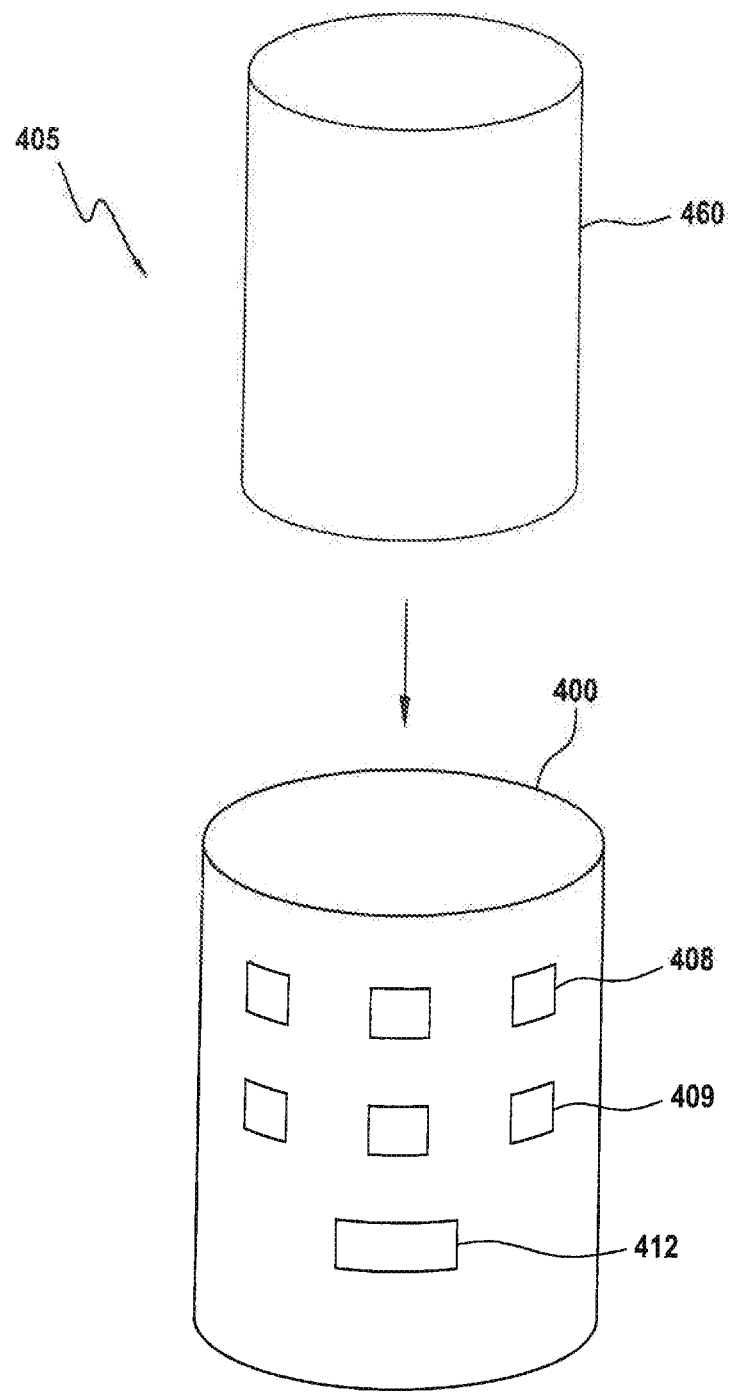
FIGS. 4A-4B show a mobile calorimeter in accordance with another embodiment.
Figure 4B:
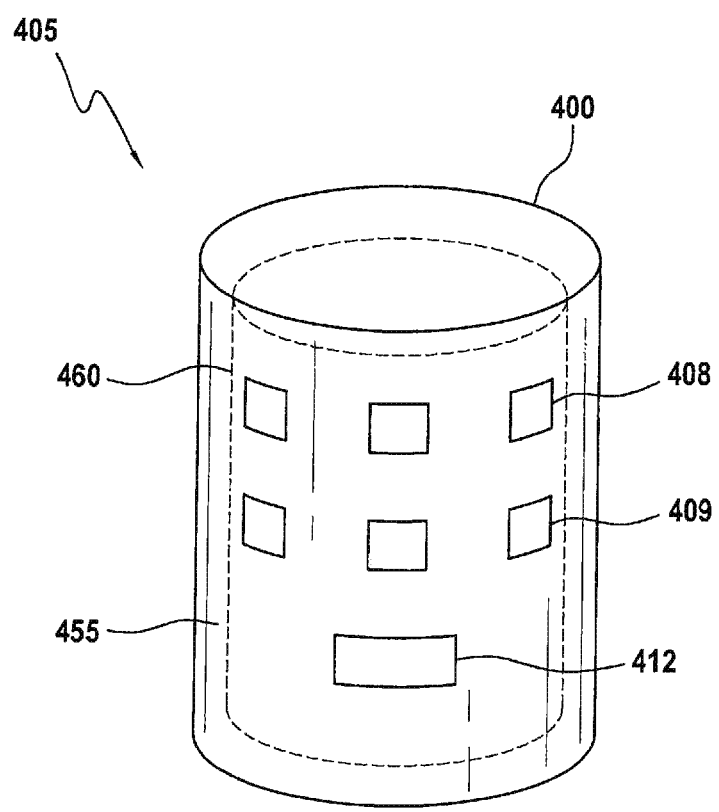

In other embodiments, a mobile calorimeter may have a different form or structure. FIGS. 4A-4B show a mobile calorimeter system in accordance with another embodiment. The mobile calorimeter system 405 includes a cylinder 460 and a mobile calorimeter 400, which includes one or more heat flow sensors 408, one or more sensors 409, and an RFID tag 412. Each heat flow sensor 408 may include a thermoelectric device such as a Peltier plate, for example. Each heat flow sensor 408 may include an MFC sensor. Mobile calorimeter 400 also includes sensors 409, which may include a variety of other types of sensors.

Referring to FIG. 4A, a portion of a batch of concrete is poured into a cylinder 460. Cylinder 460 fits into mobile calorimeter 400. After receiving the concrete, cylinder 460 is placed into mobile calorimeter 400, as shown in FIG. 4B. Cylinder 460 and mobile calorimeter 400 are separated by a small volume of air 455.

Heat flow sensors 408 detect heat flow and provide the measurements to master database module 235, for example. Sensors 409 may provide other measurements to master database module 235. In a manner similar to that described above, master database module 235 may provide the information obtained by heat flow sensors 408, and by sensors 409, to prediction module 280 and instruct prediction module 280 to generate projections of setting behavior and strength for the batch of concrete.

Advantageously, the presence of the volume of air 455 between cylinder 460 and mobile calorimeter 400 may facilitate the measurement of heat flow, and the calculation of expected performance characteristics of the concrete.

Figure 4C:
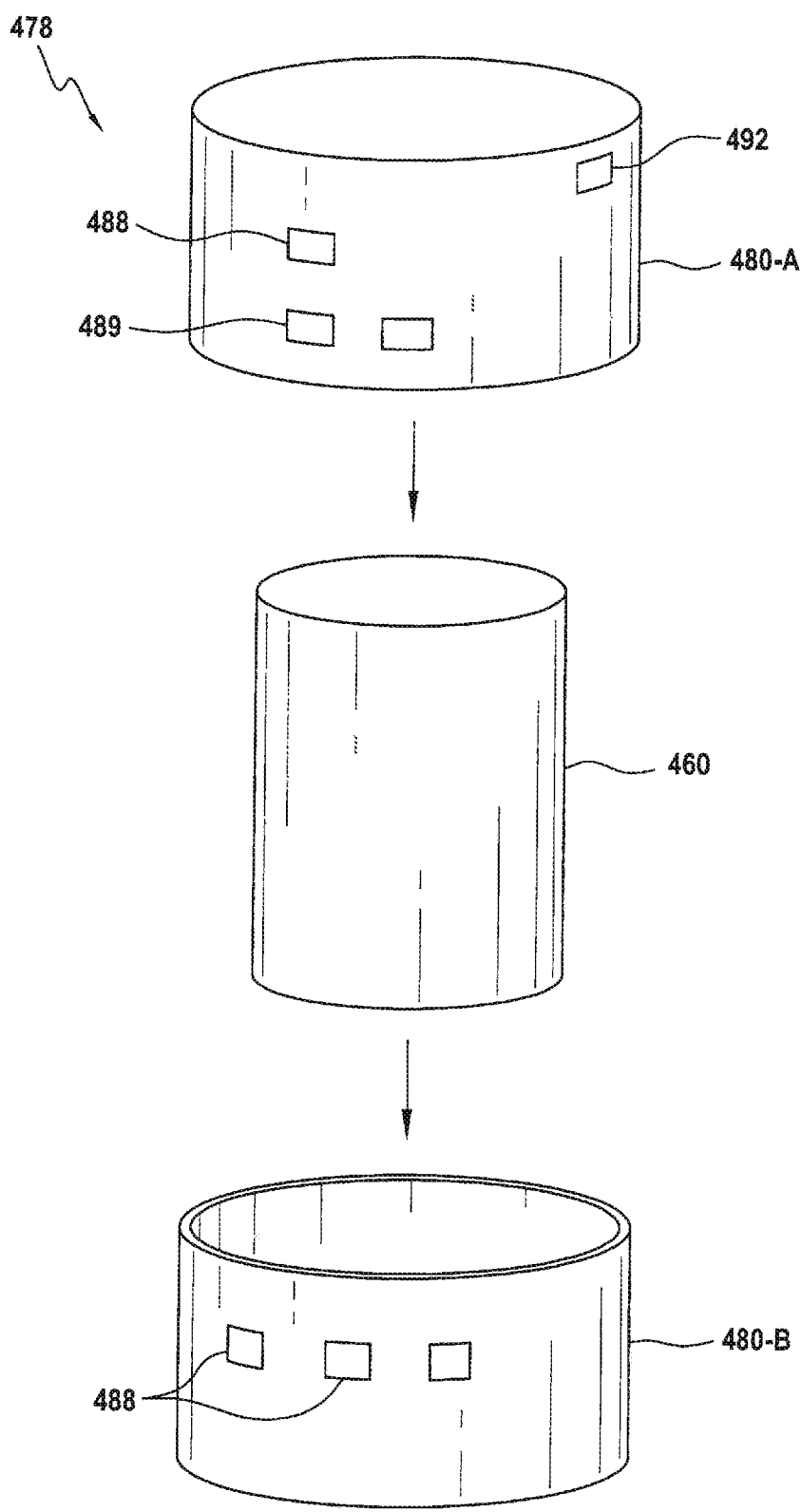
FIGS. 4C-4D show a mobile calorimeter in accordance with another embodiment.
Figure 4D:
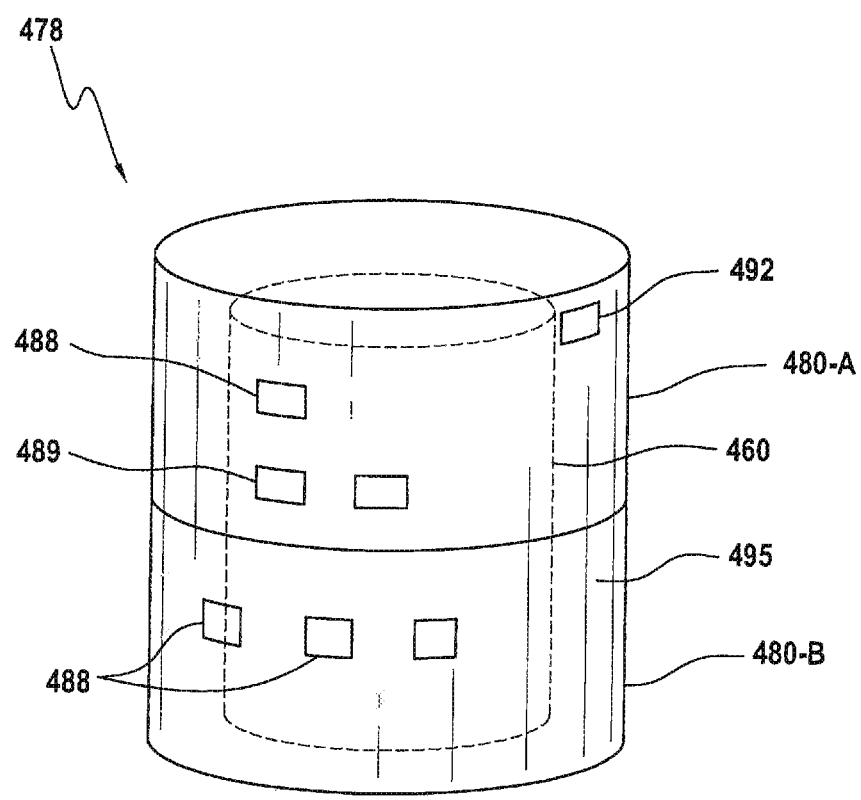

FIGS. 4C-4D show a mobile calorimeter system in accordance with another embodiment. The mobile calorimeter system 478 includes a cylinder 460, an upper cap 480-A, and a lower cap 480-B. Upper cap 480-A and/or lower cap 480-B includes one or more heat flow sensors 488, one or more sensors 489 (which may include a variety of other sensors), and an RFID tag 492. Each heat flow sensor 488 may include a thermoelectric device such as a Peltier plate, for example. Each heat flow sensor 488 may include an MFC sensor.

A portion of a batch of concrete is poured into a cylinder 460. After cylinder 460 receives the concrete, upper cap 480-A and lower cap 480-B are fitted around cylinder 460, as shown in FIG. 4D. Cylinder 460 and upper cap 480-A and lower cap 480-B are separated by a small volume of air 495.

Heat flow sensors 488 detect heat flow and provide the measurements to master database module 235, for example. Sensors 489 may provide other measurements to master database module 235. In a manner similar to that described above, master database module 235 may provide the information obtained by heat flow sensors 488, and by sensors 499, to prediction module 280 and instruct prediction module 280 to generate projections of setting behavior and strength for the batch of concrete.

In another embodiment, a heat flow sensor includes a thermoelectric device such as a Peltier plate, which is used to detect heat flow and predict the behavior of the concrete. A current may be passed through the Peltier plate, causing a vibration in the cylinder. These vibrations may modify the heat flow generated by the concrete. The modified heat flow is detected by one or more sensors and used to predict the behavior of the concrete.

In various embodiments, the method steps described herein, including the method steps described in FIGS. 3A-3B, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 3A-3B, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
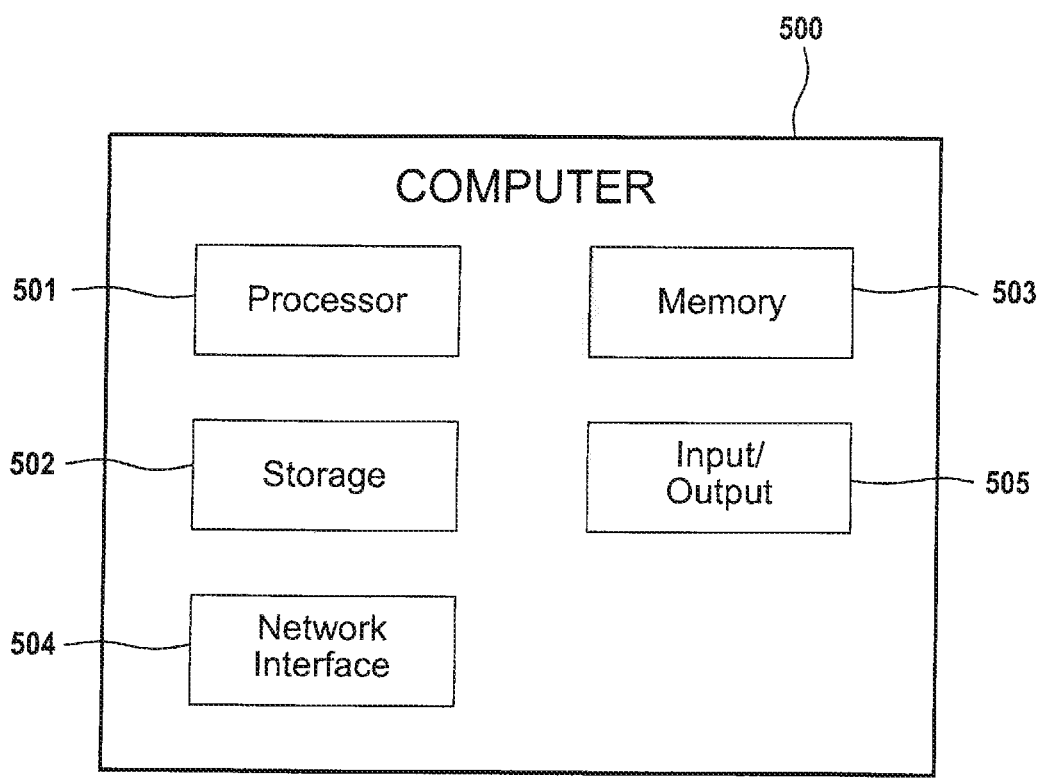
FIG. 5 shows an exemplary computer which may be used to implement certain embodiments.

A high-level block diagram of an exemplary computer that may be used to implement systems, apparatus and methods described herein is illustrated in FIG. 5. Computer 500 includes a processor 501 operatively coupled to a data storage device 502 and a memory 503. Processor 501 controls the overall operation of computer 500 by executing computer program instructions that define such operations. The computer program instructions may be stored in data storage device 502, or other computer readable medium, and loaded into memory 503 when execution of the computer program instructions is desired. Thus, the method steps of FIGS. 3A-3B can be defined by the computer program instructions stored in memory 503 and/or data storage device 502 and controlled by the processor 501 executing the computer program instructions. For example, the computer program instructions can be implemented as computer executable code programmed by one skilled in the art to perform an algorithm defined by the method steps of FIGS. 3A-3B. Accordingly, by executing the computer program instructions, the processor 501 executes an algorithm defined by the method steps of FIGS. 3A-3B. Computer 500 also includes one or more network interfaces 504 for communicating with other devices via a network. Computer 500 also includes one or more input/output devices 505 that enable user interaction with computer 500 (e.g., display, keyboard, mouse, speakers, buttons, etc.).

Processor 501 may include both general and special purpose microprocessors, and may be the sole processor or one of multiple processors of computer 500. Processor 501 may include one or more central processing units (CPUs), for example. Processor 501, data storage device 502, and/or memory 503 may include, be supplemented by, or incorporated in, one or more application-specific integrated circuits (ASICs) and/or one or more field programmable gate arrays (FPGAs).

Data storage device 502 and memory 503 each include a tangible non-transitory computer readable storage medium. Data storage device 502, and memory 503, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 505 may include peripherals, such as a printer, scanner, display screen, etc. For example, input/output devices 505 may include a display device such as a cathode ray tube (CRT) or liquid crystal display (LCD) monitor for displaying information to the user, a keyboard, and a pointing device such as a mouse or a trackball by which the user can provide input to computer 500.

Any or all of the systems and apparatus discussed herein, including computer 156, storage 178, master database module 235, cloud database 270, prediction module 280, and components thereof, may be implemented using a computer such as computer 500.

One skilled in the art will recognize that an implementation of an actual computer or computer system may have other structures and may contain other components as well, and that FIG. 5 is a high level representation of some of the components of such a computer for illustrative purposes.

Figure 6:
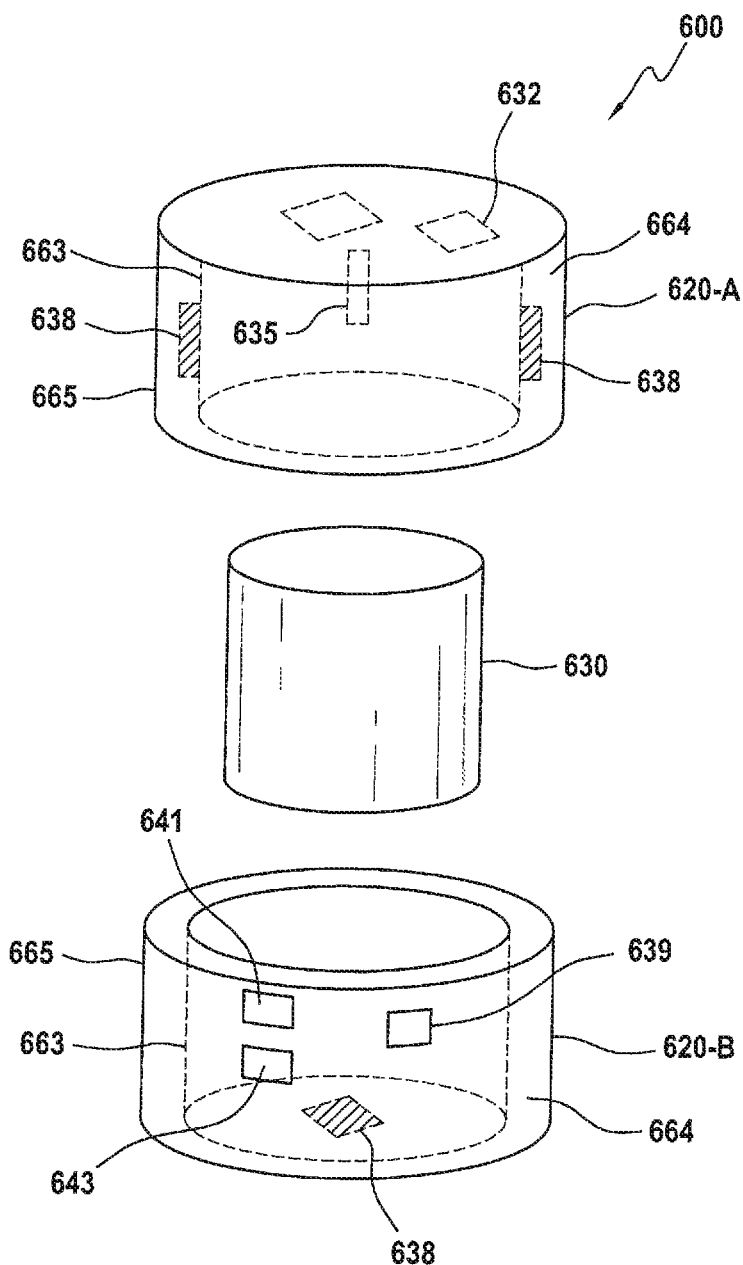
FIG. 6 shows a mobile calorimeter in accordance with another embodiment.

FIG. 6 shows a mobile calorimeter system in accordance with another embodiment. The mobile calorimeter system 600 includes a cylinder 630, an upper cap 620-A, and a lower cap 620-B. Each of upper cap 620-A and lower cap 620-B includes an inner wall 663 and an outer wall 665, separated by a volume of air 664. Advantageously, the double-walled structure and the volume of air 664 provides for heat insulation.

Mobile calorimeter system 600 includes a humidity sensor 632, a temperature sensor 635, a plurality of heat flow sensors 638, a motion sensor 641, a location detector 643, and a macro fiber composite (MFC) sensor 639. Temperature sensor 635 and humidity sensor 632 are disposed on an inside surface of upper cap 620-A. Temperature sensor 635 includes a sensor portion that protrudes from the surface and penetrates the surface of the concrete in cylinder 630, or remains proximate the surface of the concrete. Each heat flow sensor 638 is disposed on an outside surface of an inner wall of upper cap 620-A or lower cap 620-B.

Motion sensor 641 includes an accelerometer. Location detector 643 includes GPS capability. Location may be determined based on GPS data and by using triangulation.

A portion of a batch of concrete is poured into a cylinder 630. After the concrete is poured into cylinder 630, upper cap 620-A and lower cap 620-B are fitted around cylinder 630. Cylinder 630 may fit snugly into caps 620, or may fit loosely, leaving a volume of air (different from volume 664) between cylinder 630 and caps 620.

Heat flow sensors 638 detect heat flow and provide the measurements to master database module 235, for example. Humidity sensor 632 and temperature sensor 635 may provide humidity and temperature measurements to master database module 235.

In one embodiment, heat flow sensors 638 are calibrated to measure the amount of heat loss over any time period from the mobile calorimeter. Mathematically, the temperature increase inside the calorimeter multiplied by the concrete specific heat gives the heat energy retained in the calorimeter, and in combination with the heat loss computed as indicated provides a good measure of concrete hydration heat under equivalent adiabatic conditions. Thus, the mobile calorimeter may be used for field assessment of concrete adiabatic hydration heat and adiabatic temperature rise versus curing age at a particular equivalent temperature, such as 20 dC, for example. Such adiabatic profiles are known to be mixture design dependent and can thus be used to determine concrete quality and strength performance under field conditions where quality can vary by 20% or more.

In another embodiment, cylinder is placed into lower cap 620-B before concrete is poured into cylinder 630. Concrete is then poured into cylinder 630. Measurements from WC sensor 639 are transmitted to master database module 235. Measurements from WC sensor 639 are used to detect when cylinder 630 is full of concrete. When it is determined that cylinder 630 is full of concrete, master database module 235 causes the truck to stop pouring concrete. Upper cap 620-A may then be placed onto cylinder 630.

In the illustrative embodiment, data obtained by WC sensor 639 is also used to detect when mobile calorimeter system 600 is moved.

In a manner similar to that described above, master database module 235 may provide the information obtained by humidity sensor 632, temperature sensor 635, heat flow sensors 638, and MFC sensor 639, to prediction module 280 and instruct prediction module 280 to generate a prediction of a performance characteristic for the batch of concrete (e.g., projections of setting behavior and strength for the batch of concrete).

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

Furthermore, the invention as described herein, can be defined by one or more of the following items.

1. A mobile calorimeter system comprising:
a container comprising one or more walls defining a cavity, the container adapted to hold a concrete mixture within the cavity; and
one or more heat flow sensors adapted to generate data relating to a heat flow generated by the concrete mixture.

2. The mobile calorimeter system of item 1, further comprising a second container adapted to hold concrete and to fit inside the container.

3. The mobile calorimeter system of item 1, wherein the one or more heat flow sensors include one of a thermoelectric device, a Peltier plate, and a macro fiber composite (MFC) sensor.

4. The mobile calorimeter system of item 1, wherein the one or more heat flow sensors are attached to the one or more walls.

5. The mobile calorimeter system of item 1, wherein the one or more heat flow sensors are embedded within the one or more walls.

6. The mobile calorimeter system of item 1, wherein the container has one of a cylindrical shape, a cubical shape, and a rectangular shape.

7. The mobile calorimeter system of item 1, further comprising a radio frequency identification tag.

8. The mobile calorimeter system of item 1, further comprising one of a humidity sensor, a temperature sensor, a motion sensor, and a GPS-based location sensor.

9. A concrete testing system comprising:
the mobile calorimeter system of item 1;
a network; and
a processor communicatively coupled to the mobile calorimeter via the network, the processor being adapted to:
receive, via the network, the data from the one or more heat flow sensors data; and
generate a prediction of a characteristic of the concrete mixture, based on the data.

10. A method of controlling quality of one or more batches of a concrete mixture, the method comprising:
for each of a plurality of batches of concrete produced in a closed-loop production system:
pouring a portion of the respective batch of concrete into a mobile calorimeter that comprises a heat flow sensor and a radio-frequency identification device (RFID);
receiving from the RFID an identifier associated with the respective mobile calorimeter;
receiving from the heat flow sensor a signal indicating that the mobile calorimeter is full of concrete;
receiving from the heat flow sensor one or more measurements of heat flow;
determining data defining an expected setting behavior and an expected strength of the respective batch of concrete based on the one or more measurements of heat flow; and
storing the one or more measurements of heat flow and the data in association with the identifier.

11. The method of item 10, wherein the heat flow sensor includes one of a thermoelectric device, a Peltier plate, and a macro fiber composite (MFC) sensor.

12. The method of item 10, wherein the mobile calorimeter comprises a container having one of a cylindrical shape, a cubical shape, and a rectangular shape.

13. The method of item 11, wherein the mobile calorimeter comprises one or more walls;
wherein the heat flow sensor is disposed on the one or more walls.

14. The method of item 10, wherein the mobile calorimeter further comprises one of a humidity sensor, a temperature sensor, a motion sensor, a location sensor.

15. The method of item 14, wherein the mobile calorimeter comprises a location sensor,
the method further comprising:
receiving location data from the location sensor; and
determining a location of the mobile calorimeter based on the location data.

16. A method of testing a performance of a batch of concrete, the method comprising:
using a heat flow sensor to obtain a measure of heat flow generated by a quantity of concrete, the quantity of concrete being obtained from a batch of concrete; and
determining a measure of an expected performance of the batch of concrete, based on the measure of heat flow.

17. The method of item 16, further comprising:
pouring the quantity of concrete into a mobile calorimeter that comprises the heat flow sensor.

18. The method of item 16, wherein the mobile calorimeter further comprises a radio-frequency identification device (RFID);
the method further comprising:
receiving from the RFID an identifier associated with the mobile calorimeter.

19. The method of item 18, further comprising:
receiving, by a processor, from the heat flow sensor, the measure of heat flow;
determining data defining an expected setting behavior and an expected strength of the batch of concrete based on the measure of heat flow.

20. The method of item 19, further comprising:
storing the identifier and the measure of heat flow.

21. An apparatus comprising:
a first cylindrical wall having a first radius, the first cylindrical wall having an exterior surface;
a second cylindrical wall having a second radius greater than the first radius;
a first end portion having an interior surface, the first end portion being solid with no opening that passes therethrough; and
a second end portion, the second end portion being solid with no opening that passes therethrough;
wherein:
a first volume is defined by the first cylindrical wall, the first end portion and the second end portion, the first volume being adapted to hold a concrete test cylinder; and
a second volume is defined between the first and second cylindrical walls;
the apparatus further comprising:
a temperature sensor disposed on the interior surface of the first end portion, wherein the temperature sensor protrudes from the interior surface and does not penetrate the first end portion, the temperature sensor being adapted to:
penetrate an exposed surface of a concrete mixture in the concrete test cylinder; and obtain a measurement of temperature of the concrete mixture; and one or more heat flow sensors disposed on the exterior surface of the first cylindrical wall, in the second volume between the first and second walls, wherein each of the one or more heat flow sensors is separated from the concrete mixture disposed in the first volume by the first wall.

22. The apparatus of item 21, wherein the one or more heat flow sensors include one of a thermoelectric device, a Peltier plate, and a macro fiber composite (MFC) sensor.

23. The apparatus of item 21, further comprising a radio frequency identification tag.

24. The apparatus of item 21, further comprising one of a humidity sensor, a motion sensor, and a GPS-based location sensor.

25. A concrete testing system comprising:
the apparatus of item 21;
a network; and
a processor communicatively coupled to the measurement system via the network, the processor being adapted to:
receive, via the network, the data from the one or more heat flow sensors; and
generate a prediction of a characteristic of the concrete mixture, based on the data.

26. An apparatus comprising:
a first wall;
a top portion, the top portion being solid with no opening that passes therethrough; and
a bottom portion, the bottom portion being solid with no opening that passes therethrough;
wherein the first wall, the top portion, and the second portion enclose a first volume adapted to hold a concrete test cylinder;
the apparatus further comprising:
a second wall enclosing the first wall, wherein the first and second walls define a second volume; and
a heat flow sensor disposed in the second volume, wherein the heat flow sensor is separated from the first volume by the first wall.

27. The apparatus of item 26, wherein:
the first wall comprises an interior surface and an exterior surface;
the heat flow sensor is disposed on the exterior surface.

28. The apparatus of item 26, wherein the first volume is adapted to hold one of a standard 4×8-inch concrete test cylinder and a standard 6×12-inch concrete test cylinder.

29. A measuring device comprising:
a first wall;
a top portion; and
a bottom portion;
wherein the first wall, the top portion, and the second portion enclose a first volume;
the measuring device further comprising:
a second wall enclosing the first wall, wherein the first and second walls define a second volume; and
a heat flow sensor disposed in the second volume.

30. The measuring device of item 29, wherein:
the first wall comprises an interior surface and an exterior surface;
the heat flow sensor is disposed on the exterior surface.

31. The measuring device of item 29, wherein the first volume is adapted to hold one of a standard 4×8-inch concrete test cylinder and a standard 6×12-inch concrete test cylinder.

32. An apparatus comprising:
a first cylindrical wall having a first radius;
a second cylindrical wall having a second radius greater than the first radius;
a first end portion having an interior surface, the first end portion being solid with no opening that passes therethrough; and
a second end portion, the second end portion being solid with no opening that passes therethrough;
wherein:
a first volume is defined by the first cylindrical wall, the first end portion and the second end portion, the first volume being adapted to hold a concrete test cylinder; and
a second volume is defined between the first and second cylindrical walls;
the apparatus further comprising:
a temperature sensor disposed on the interior surface of the first end portion, wherein the temperature sensor protrudes from the interior surface and does not penetrate the first end portion, the temperature sensor being adapted to obtain a measurement of temperature of the concrete mixture; and
one or more heat flow sensors disposed in the second volume between the first and second walls, wherein each of the one or more heat flow sensors is separated from the concrete mixture disposed in the first volume by the first wall.

33. The apparatus of item 32, wherein the one or more heat flow sensors include one of a thermoelectric device, a Peltier plate, and a macro fiber composite (MFC) sensor.

34. The apparatus of item 32, further comprising a radio frequency identification tag.

35. The apparatus of item 32, further comprising one of a humidity sensor, a motion sensor, and a GPS-based location sensor.

36. The apparatus of item 32, wherein the first volume is adapted to hold one of a standard 4×8-inch concrete test cylinder and a standard 6×12-inch concrete test cylinder.

37. A concrete testing system comprising: the apparatus of item 32;
a network; and
a processor communicatively coupled to the measurement system via the network, the
processor being adapted to:
receive, via the network, the data from the one or more heat flow sensors; and
generate a prediction of a characteristic of the concrete mixture, based on the data.

38. An apparatus comprising:
a first cylindrical wall having a first radius;
a second cylindrical wall having a second radius greater than the first radius;
a first end portion having an interior surface, the first end portion being solid with no opening that passes therethrough; and
a second end portion, the second end portion being solid with no opening that passes therethrough;
wherein:
a first volume is defined by the first cylindrical wall, the first end portion and the second end portion, the first volume being adapted to hold a concrete test cylinder; and
a second volume is defined between the first and second cylindrical walls, the second volume holding a quantity of air;

the apparatus further comprising:
a temperature sensor disposed on the interior surface of the first end portion, wherein the temperature sensor protrudes from the interior surface and does not penetrate the first end portion, the temperature sensor being adapted to obtain a measurement of temperature of the concrete mixture.

39. The apparatus of item 38, further comprising a radio frequency identification tag.

40. The apparatus of item 38, further comprising one of a humidity sensor, a motion sensor, and a GPS-based location sensor.

41. The apparatus of item 38, wherein the first volume is adapted to hold one of a standard 4×8-inch concrete test cylinder and a standard 6×12-inch concrete test cylinder.

The invention claimed is:

1. An apparatus comprising:
a first cylindrical wall having a first radius;
a second cylindrical wall having a second radius greater than the first radius;
a first end portion having an interior surface, the first end portion being solid with no opening that passes therethrough; and
a second end portion, the second end portion being solid with no opening that passes therethrough;
wherein:
a first volume is defined by the first cylindrical wall, the first end portion and the second end portion, the first volume being adapted to hold a concrete test cylinder; and
a second volume is defined between the first and second cylindrical walls;
the apparatus further comprising:
a temperature sensor disposed on the interior surface of the first end portion, wherein the temperature sensor protrudes from the interior surface and does not penetrate the first end portion, the temperature sensor being adapted to obtain a measurement of temperature of the concrete mixture; and
one or more heat flow sensors disposed in the second volume between the first and second walls, wherein each of the one or more heat flow sensors is separated from the concrete mixture disposed in the first volume by the first wall.

2. The apparatus of claim 1, wherein the one or more heat flow sensors include one of a thermoelectric device, a Peltier plate, and a macro fiber composite (MFC) sensor.

3. The apparatus of claim 1, further comprising a radio frequency identification tag.

4. The apparatus of claim 1, further comprising one of a humidity sensor, a motion sensor, and a GPS-based location sensor.

5. The apparatus of claim 1, wherein the first volume is adapted to hold one of a standard 4×8-inch concrete test cylinder and a standard 6×12-inch concrete test cylinder.

6. A concrete testing system comprising:
the apparatus of claim 1;
a network; and
a processor communicatively coupled to the measurement system via the network, the processor being adapted to:
receive, via the network, the data from the one or more heat flow sensors; and
generate a prediction of a characteristic of the concrete mixture, based on the data.

7. An apparatus comprising:
a first cylindrical wall having a first radius;
a second cylindrical wall having a second radius greater than the first radius;
a first end portion having an interior surface, the first end portion being solid with no opening that passes therethrough; and
a second end portion, the second end portion being solid with no opening that passes therethrough;
wherein:
a first volume is defined by the first cylindrical wall, the first end portion and the second end portion, the first volume being adapted to hold a concrete test cylinder; and
a second volume is defined between the first and second cylindrical walls, the second volume holding a quantity of air;
the apparatus further comprising:
a temperature sensor disposed on the interior surface of the first end portion, wherein the temperature sensor protrudes from the interior surface and does not penetrate the first end portion, the temperature sensor being adapted to obtain a measurement of temperature of the concrete mixture.

8. The apparatus of claim 7, further comprising a radio frequency identification tag.

9. The apparatus of claim 7, further comprising one of a humidity sensor, a motion sensor, and a GPS-based location sensor.

10. The apparatus of claim 7, wherein the first volume is adapted to hold one of a standard 4×8-inch concrete test cylinder and a standard 6×12-inch concrete test cylinder.

* * * * *